US006805118B2

(12) United States Patent
Brooker et al.

(10) Patent No.: US 6,805,118 B2
(45) Date of Patent: *Oct. 19, 2004

(54) PULMONARY DOSING SYSTEM AND METHOD

(75) Inventors: Michael J. Brooker, Westerville, OH (US); John E. Frye, Groveport, OH (US); Paul T. Kotnik, Powell, OH (US); Michael B. Mosholder, Columbus, OH (US); Michael E. Placke, Columbus, OH (US); William C. Zimlich, Jr., Dublin, OH (US)

(73) Assignee: Zivena, Inc., Columbus, OH (US)

( * ) Notice: Subject to any disclaimer, the term of this patent is extended or adjusted under 35 U.S.C. 154(b) by 68 days.

This patent is subject to a terminal disclaimer.

(21) Appl. No.: 09/921,331

(22) Filed: Aug. 2, 2001

(65) Prior Publication Data

US 2002/0026940 A1 Mar. 7, 2002

Related U.S. Application Data

(63) Continuation of application No. 09/263,986, filed on Mar. 5, 1999, now Pat. No. 6,269,810.
(60) Provisional application No. 60/076,962, filed on Mar. 5, 1998.

(51) Int. Cl.[7] ..................... A61M 15/00; A61M 16/10
(52) U.S. Cl. ..................... 128/203.12; 128/200.21; 128/203.29
(58) Field of Search ............... 128/200.14, 200.16, 128/200.18, 200.21, 200.22, 203.12, 203.18, 203.24, 203.25, 203.29, 205.12, 909

(56) References Cited

U.S. PATENT DOCUMENTS 90,051 A 5/1869 Rogers

| 2,521,084 A | | 9/1950 | Oberto |
|---|---|---|---|
| 3,037,501 A | | 6/1962 | Miller |
| 3,301,255 A | | 1/1967 | Thompson |
| 3,565,072 A | | 2/1971 | Gauthier |
| 3,915,165 A | | 10/1975 | Rambosek et al. |
| 4,106,503 A | | 8/1978 | Rosenthal et al. |
| 4,244,361 A | * | 1/1981 | Neubert ............... 128/200.14 |
| 4,257,415 A | * | 3/1981 | Rubin ................. 128/200.21 |
| 4,343,304 A | * | 8/1982 | Hickmann ............ 128/200.14 |
| 4,360,018 A | | 11/1982 | Choksi |
| 4,440,165 A | | 4/1984 | Holzel |

(List continued on next page.)

FOREIGN PATENT DOCUMENTS

| DE | 36 36 669 A1 | 5/1988 |
|---|---|---|
| EP | 0 042 468 A1 | 2/1981 |
| EP | 0 302 958 B1 | 8/1987 |
| EP | 0 533 409 A1 | 3/1993 |
| WO | WO 92/12750 | 8/1992 |

*Primary Examiner*—Henry Bennett
*Assistant Examiner*—Andrea M. Ragonese
(74) *Attorney, Agent, or Firm*—Frost Brown Todd LLC

(57) ABSTRACT

A pulmonary dosing system and method for supplying to a patient a predetermined amount of respirable therapeutically active material. The system comprises a patient interface to introduce the material into the patient's lungs. The patient interface is connected to a flexible inhalation tube and a flexible exhalation tube. The exhalation tube is connected to a filter having an outlet connected to atmosphere. The inhalation tube is connected to an apparatus for providing pulsed amounts of the material entrained in filtered atmospheric air. A control unit operates the pulmonary dosing system in accordance with operator inputs regarding the number of patent exhales between pulses, and pulse length. The exhaust filter and the apparatus for providing pulsed amounts of the therapeutically active material may be enclosed in a containment case and the patient's interface may comprise a mouth tube-mask combination when the therapeutically active material comprises at least one toxic drug.

48 Claims, 8 Drawing Sheets

U.S. PATENT DOCUMENTS

| | | | |
|---|---|---|---|
| 4,452,239 A | | 6/1984 | Malem |
| 4,470,413 A | * | 9/1984 | Warncke ................ 128/201.18 |
| 4,513,741 A | | 4/1985 | Demi |
| 4,558,710 A | | 12/1985 | Eichler |
| 4,559,940 A | | 12/1985 | McGinnis |
| 4,573,463 A | | 3/1986 | Hall |
| 4,592,348 A | | 6/1986 | Waters, IV et al. |
| 4,649,911 A | | 3/1987 | Knight et al. |
| 4,653,493 A | | 3/1987 | Hoppough |
| 4,674,492 A | | 6/1987 | Niemeyer |
| 4,719,911 A | | 1/1988 | Carrico |
| 4,795,330 A | | 1/1989 | Noakes et al. |
| 4,819,629 A | | 4/1989 | Jonson |
| 4,823,784 A | | 4/1989 | Bordoni et al. |
| 4,826,510 A | | 5/1989 | McCombs |
| 4,832,012 A | | 5/1989 | Raabe et al. |
| 4,883,051 A | | 11/1989 | Westenskow et al. |
| 4,971,052 A | | 11/1990 | Edwards |
| 5,022,587 A | * | 6/1991 | Hochstein ................ 239/72 |
| 5,036,840 A | | 8/1991 | Wallace |
| 5,080,093 A | | 1/1992 | Raabe et al. |
| 5,099,833 A | | 3/1992 | Michaels |
| 5,148,802 A | * | 9/1992 | Sanders et al. ........ 128/204.18 |
| 5,156,776 A | | 10/1992 | Loedding et al. |
| 5,178,138 A | | 1/1993 | Walstrom et al. |
| 5,287,849 A | * | 2/1994 | Piper et al. ............ 128/203.12 |
| 5,299,565 A | * | 4/1994 | Brown ................ 128/200.21 |
| 5,320,108 A | | 6/1994 | Cloutier |
| 5,322,057 A | * | 6/1994 | Raabe et al. ............ 128/203.12 |
| 5,364,615 A | | 11/1994 | Debs et al. |
| 5,372,126 A | | 12/1994 | Blau |
| 5,479,920 A | * | 1/1996 | Piper et al. ............ 128/204.23 |
| 5,487,378 A | | 1/1996 | Robertson et al. |
| 5,560,353 A | * | 10/1996 | Willemot et al. ...... 128/204.21 |
| 5,570,682 A | * | 11/1996 | Johnson ................ 128/200.14 |
| 5,655,516 A | | 8/1997 | Goodman et al. |
| 5,697,364 A | | 12/1997 | Chua et al. |
| 5,771,882 A | | 6/1998 | Psaros et al. |
| 5,803,065 A | * | 9/1998 | Zdrojkowski et al. . 128/204.23 |
| 5,803,078 A | * | 9/1998 | Brauner ................ 128/207.14 |
| 5,813,397 A | | 9/1998 | Goodman et al. |
| 5,848,587 A | | 12/1998 | King |
| 5,865,173 A | * | 2/1999 | Froehlich ................ 128/204.23 |
| 5,970,975 A | * | 10/1999 | Estes et al. ............ 128/204.23 |
| 5,983,896 A | | 11/1999 | Fukunaga et al. |
| 6,029,664 A | * | 2/2000 | Zdrojkowski et al. . 128/204.23 |
| 6,076,520 A | * | 6/2000 | Cooper ................ 128/200.21 |
| 6,269,810 B1 | * | 8/2001 | Brooker et al. ........ 128/203.12 |

* cited by examiner

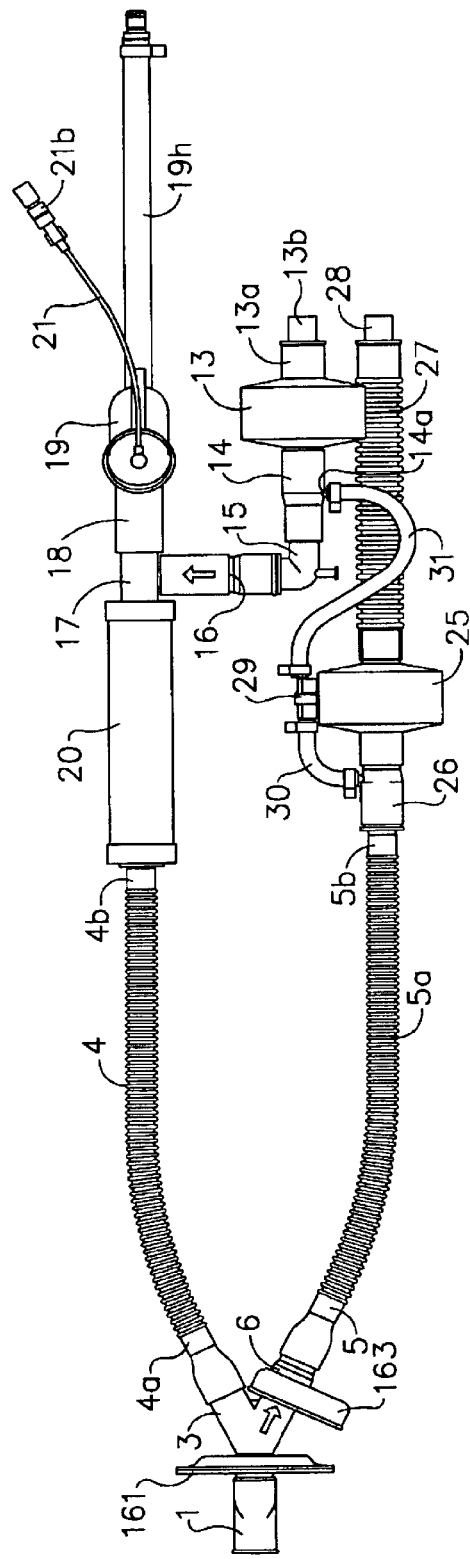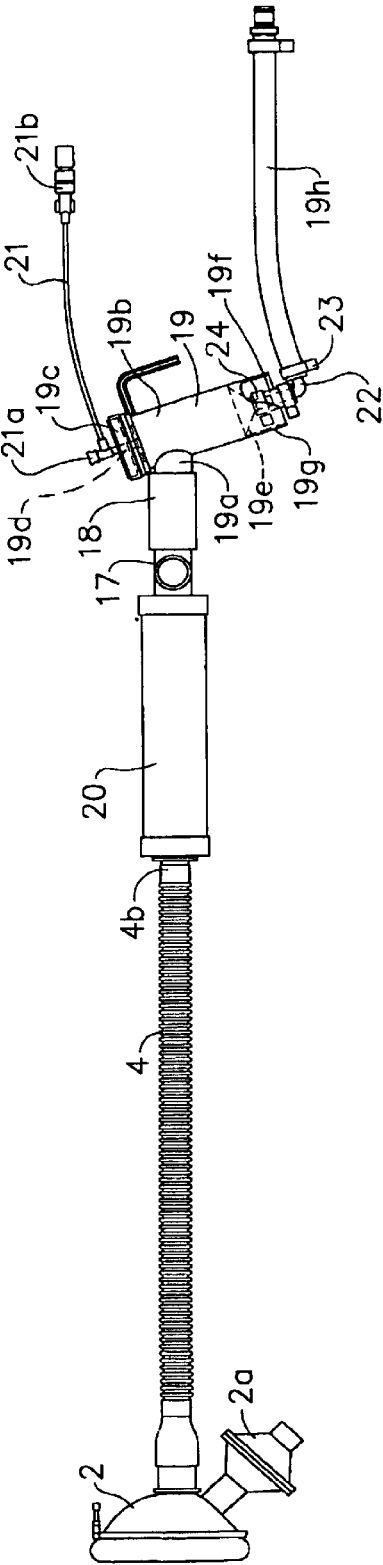
FIG. 2
FIG. 3

PULMONARY DOSING SYSTEM AND METHOD

This is a continuation of U.S. patent application Ser. No. 09/263,986, filed Mar. 5, 1999 now issued as U.S. Pat. No. 6,269,810.

TECHNICAL FIELD

This application is based on U.S. Provisional Patent Application Ser. No. 60/076,962, Pulmonary Dosing System and Method, Michael J. Brooker, et al., filed Mar. 5, 1998.

The invention relates to a pulmonary dosing system and method for supplying to a patient a predetermined amount of respirable therapeutically active material entrained in filtered atmospheric air, and more particularly to such a system and method which is compact, self-contained, and capable of supplying any respirable therapeutically active material including toxic drugs such as chemotherapy drugs.

BACKGROUND ART

Prior art workers have devised a number of different systems for delivering respirable therapeutically active material intended for use in conjunction with mechanical respirators, ventilators, or breathing machines. The present invention, on the other hand, is directed to a pulmonary dosing system for supplying a patient with a predetermined amount of respirable therapeutically active material, the patient being capable of normal inhalation and exhalation, on his own.

The pulmonary dosing system of the present invention is able to contain the therapeutically active material or drug to the extent that it can safely administer toxic drugs such as chemotherapy drugs.

The respirable therapeutically active material is entrained in pulses of air synchronized with the patient's exhalations. Except for the inhalation tube, the exhalation tube and the patient interface connected thereto, the remainder of the inhalation and exhalation portions of the system including the delivery apparatus for the therapeutically active material are located in a sealed containment case. The containment case is subjected to a mild vacuum from a vacuum source including a filter to further assure containment of the therapeutically active material, if necessary. The system is provided with a control unit containing a compressor and valve to provide pulsed air, a vacuum pump to provide the mild vacuum within the containment case, and a computer with inputs from various sensor devices together with a number of interfaces with the operator and with the patient.

One of the more advantageous features of the drug delivery or pulmonary dosing system is its efficiency in delivering drugs. This may be particularly important with respect to the time spent by the patient and the support staff for each treatment and also with respect to reducing the expense of extremely costly drugs. The efficiency refers not only to the efficiency of delivering drug to the patient (not lost in the delivery system), but also to the efficiency of getting the delivered drug to penetrate deep into the lung of the patient to provide the needed therapy. The present invention reduces the amount of aerosolized drug that may be deposited in the mouth, the upper airway, or the nasal cavity.

One of the novel features which adds to this efficiency is the combination of the nebulizer (or other aerosol-producing device), the plenum, an air supply and the control system which are combined to provide a metered dose of drug and air to the patient at the designated time for inhalation. In one efficient operation, the aerosol-producing device is controlled to deliver a selected volume of drug aerosol to the plenum prior to the inhalation phase of the patient. As described herein, this is advantageously performed by sensing the exhalation phase of the patient and then providing a pulse of air to the nebulizer which results in a metered volume of aerosolized drug in the plenum.

It is an object of the present invention to provide a pulmonary dosing system for supplying to a patient capable of normal breathing a predetermined amount of respirable therapeutically active material.

It is an object of the present invention to provide a dosing system connectable by a power cord to a source of electricity of standard hospital voltage and which is otherwise completely self-contained.

It is an object of the present invention to provide a delivery system wherein that portion of the system between the inhalation and exhalation tubes and their interface with the patient and a control unit are maintained in a containment case to preclude escape or leakage of the respirable therapeutically active material being dispensed to the patient.

It is an object of the present invention to provide a control unit containing a compressor together with a pulsing valve, a vacuum pump to maintain the containment case under a mild vacuum, a computer having interfaces with both the operator and the patient, the operator interfaces enabling the operator to set the number of exhalations between air pulses, the duration of each air pulse, and the amount of the respirable therapeutically active material to be dispensed.

It is an object of the present invention to provide a system capable of supplying at least one non-toxic drug to the patient.

It is an object of the present invention to provide a system capable of dispensing at least one toxic drug to the patient.

It is an object of the present invention to provide an interface between the patient and the inhalation and exhalation tubes in the form of a mouthpiece constituting a part of a mask, the mask further having an outlet leading to a filter in case the patient coughs.

DISCLOSURE OF THE INVENTION

According to the invention there is provided a pulmonary dosing system and method for supplying to a patient a predetermined amount of respirable therapeutically active material. The system comprises a patient interface to introduce the material into the patient's lungs. This interface may constitute a mouth tube, a mask and mouth tube combination, a trachea tube, a nasal tube, or the like. The patient interface is connected to a flexible inhalation tube and a flexible exhalation tube. The exhalation tube is connected to a filter, the outlet of which is connected to atmosphere. The inhalation tube is connected to an apparatus for providing pulsed amounts of the material entrained in filtered atmospheric air. Preferably, the apparatus comprises a nebulizer having an inlet for pulsed air, a plenum chamber and a connection, provided with a filter, to atmospheric air.

A control system is provided to operate the pulmonary dosing system in accordance with operator inputs selecting the number of patient exhales between pulses, the pulse length, and the amount of material to be dispensed to the patient. The exhaust filter and the apparatus for providing pulsed amounts of the therapeutically active material may be enclosed in a containment case. The dosing system is capable of supplying at least one non-toxic drug, or at least one toxic drug to the patient.

BRIEF DESCRIPTION OF THE DRAWINGS

FIG. 2 is a plan view illustrating the inhalation and exhalation elements of the system of the present invention.

FIG. 3 is a fragmentary elevational view showing the nebulizer and the plenum chamber of the present invention.

DETAILED DESCRIPTION OF THE INVENTION

Throughout this specification the word "drug" is used. This word should be interpreted to include any appropriate respirable, therapeutically active material.

For purposes of an exemplary showing, the invention will be described in an embodiment for dispensing chemotherapy drugs. While the invention is particularly useful with toxic drugs, it is by no means intended to be so limited. Again, the invention is capable of dispensing any appropriate respirable therapeutically active material.

The drug dispensed can be a solid, a liquid or a gas. For example, a dry powder inhaler could be used as the apparatus for providing a pulse of respirable therapeutically active material (i.e. the powder). A solid drug could be dissolved or suspended in a liquid carrier and aerosolized. A gaseous drug can also be delivered. A liquid drug can be comminuted or aerosolized in any conventional manner, for example, using pneumatic, electrostatic or ultrasonic devices, as are well known in the art.

Figure 1:
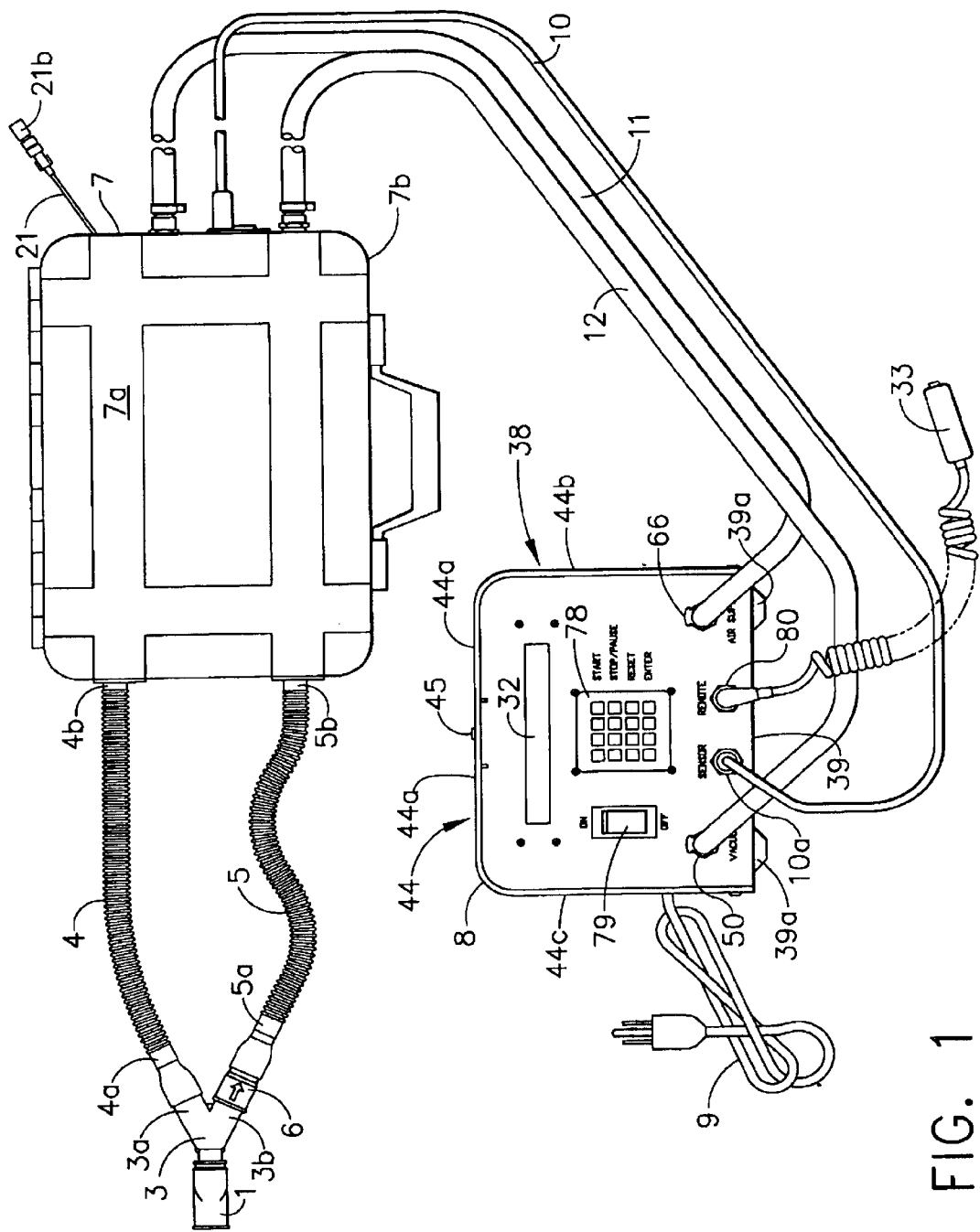
FIG. 1 is a simplified representation of the pulmonary dosing system of the present invention.

In the Figures, like parts have been given like index numerals. Reference is first made to FIG. 1 which illustrates the overall structure of the pulmonary dosing system of the present invention. The system includes a patient mouthpiece 1 to assist in containment of the aerosolized drug. The mouthpiece 1 may have, associated therewith, a mask 2, serving as an additional drug containment device. The mask is provided with a filter 2a through which air would pass should the patient cough. The filter 2a would trap aerosolized drug. The outlet of the filter 2a may lead directly to the ambient air, or it may be connected to the exhaust portion of the pulmonary dosing system.

The mouthpiece 1 is attached to a Y-adapter 3, having divergent legs 3a and 3b. An inhalation tube 4 is provided with an end 4a connected to the Y-adapter leg 3a. Similarly, an exhalation tube 5 has an end 5a connected to a check valve 6. The check valve 6, in turn, is connected to the leg 3b of Y-adapter 3. The purpose of the check valve is to assure that the patient will receive, via mouthpiece 1, only air and aerosolized drug from inhalation tube 4. It will be understood by one skilled in the art that the mouthpiece 1 could be replaced by a trachea tube (not shown), as is well known in the art.

When a mask is used, it will be provided with an inhalation tube and an exhalation tube joined to the mask. This may be accomplished, for example, by a mouth piece in a manner similar to that illustrated in FIG. 2. The mask will surround the nose and mouth area of the user's face.

Figure 4:
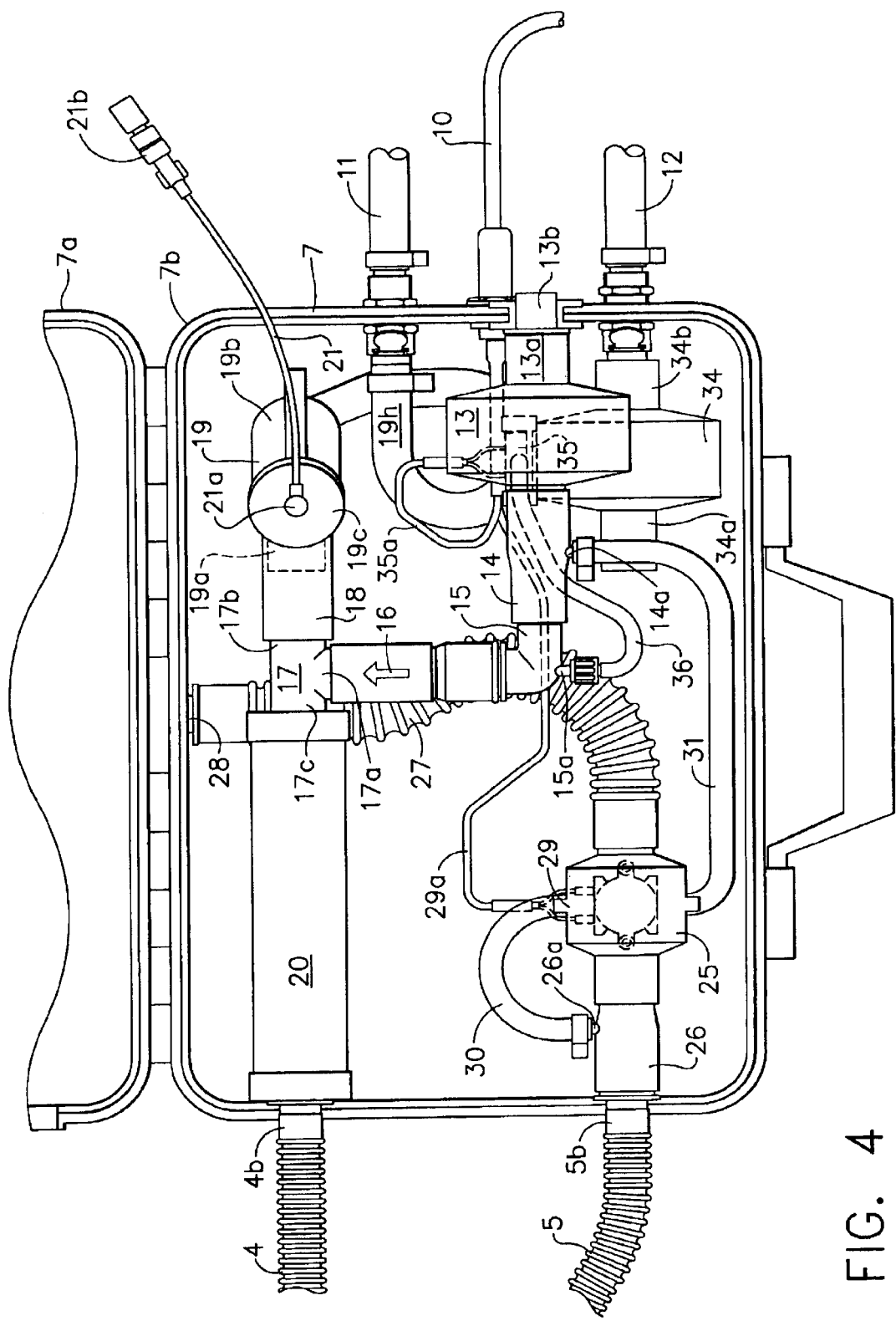
FIG. 4 is a plan view illustrating most of the inhalation and exhalation elements located in a containment case.

End 4b of inhalation tube 4 and end 5b of exhalation tube 5 are connected to adapters which pass in sealed fashion through ports in one end of a containment case 7, having a body 7a and a lid 7b (see FIG. 4). The lengths of inhalation tube 4 and exhalation tube 5 should be such as to allow a patient to sit or lie comfortably in close proximity to containment case 7.

Containment case 7 has therein a filter and an exhaust port connected to exhalation line 5. Containment box 7 also has an ambient air inlet port and filter in conjunction with a nebulizer and a plenum chamber to provide the inhalation line 4 and mouthpiece 5 with ambient air containing an aerosolized drug. All of these elements will be described in detail hereinafter.

Finally, the pulmonary dosing system of the present invention is provided with a control unit 8 connectable by power cord 9 to a source of electricity of standard hospital voltage (i.e. 115 volts, 15 amps and 60 cycles). The control unit 8 is connected to the containment case 7 by a sensor output cable 10, a pulsed air line 11 and a vacuum line 12, to be described in detail hereinafter.

Reference is now made to FIG. 2 which illustrates the inhalation and exhalation elements located within containment case 7. An inspired air filter 13 has an inlet 13a connected to a fitting 13b which passes through the containment case 7 in sealed fashion and forms an inlet port for ambient air (see also FIG. 4). The filter 13 is a standard HME filter capable of removing viruses, bacteria, etc. It will be remembered that the pulmonary dosing system of the present invention does not include a respirator or the like, and is intended for use with patients who can breathe normally.

Filter 13 has an outlet 13c adapted to receive a connector 14. The connector 14 leads to an elbow connector 15 which, in turn, leads to a check valve indicated by arrow 16. Check valve 16 is connected to the center port 17a of a T-connector 17. Another port 17b of T-connector 17 is connected by fitting 18 to the outlet 19a of an apparatus for providing a pulse of respirable drug, in this example a nebulizer 19. The third port 17c of T-fitting 17 is connected to a plenum chamber 20. The end 4b of inhalation tube 4 is connected by appropriate fitting means to the other end of plenum chamber 20, through an opening in the side wall of the containment case 7 in sealed fashion.

Reference is now made to FIG. 3 wherein the nebulizer 19, the T-fitting 17 and the plenum chamber 20 are more clearly shown. The nebulizer 19 has a cylindrical body 19b from which the outlet 19a extends. At its upper end, the nebulizer body 19b has top 19c which is fixedly sealed in place by an appropriate adhesive such as a silicone sealant. Top 19c has a central bore 19d into which one end 21a of an extension set 21 is fixed and sealed with an appropriate adhesive. The other end of extension set 21 is provided with a valve port 21b for the receipt of drug from a syringe pump, a hand syringe, or the like. Thus, the extension set 21 is the means by which medicine is introduced into nebulizer 19. Other means may be used, if desired.

The nebulizer bottom 19e slopes downwardly and inwardly to an integral, tube-like inlet 19f. The conical bottom 19e and tube-like inlet 19f are surrounded by a cylindrical skirt 19g comprising an integral, one-piece part of the nebulizer body 19b. One end of a tube 19h is attached to an elbow connector 22 by a tubing clamp 23. The elbow connector 22, in turn, is connected to nebulizer inlet 19f, again by a tubing clamp 24. The free end of tube 19h is attached through the end of containment case 7 to the pulsed air line 11 (see FIG. 4).

As previously stated above with respect to FIG. 2, the outlet 19a of nebulizer 19 is attached to port 17b of T-fitting 17 by connector 18 (see FIG. 4). Port 17c of T-connector 19 is attached to one end of plenum chamber 20. The end 4b of inhalation tube 4 is attached to the other end of plenum chamber 20 via an appropriate filling.

The nebulizer 19 is made of materials which conform to biocompatibility standards ISO 10993. If chemotherapy drugs are used, the nebulizer 19 should be able to withstand exposure to such drugs. The nebulizer 19 is preferably capable of atomizing such drugs to a particle size distribution of 1 to 5 microns, with an output volume of 0.1 to 1.0 milliliter per minute.

In the embodiment being described, it is preferred that the fitting 21b at the free end of extension set 21 be connected to a syringe pump (not shown). The syringe pump, in conjunction with the extension set 21, provides a closed, needleless delivery system by which the chemotherapy drugs can be transferred easily and safely into nebulizer 19. This closed system should be able to withstand 54 plus 10% psi back pressure during operation. The air pulses to the nebulizer from the pulsed air system are at 54 psi and the additional 10% back pressure constitutes a safety margin.

As indicated above, in the embodiment described, delivering a toxic drug, the patient interface for the drug nebulizer should be either a trachea tube or a mouth tube, preferably with a mask.

Depending on the nature of the drug being dispensed (i.e. toxic, non-toxic, etc.) the patient interface may comprise a plain mask, a plain mouth tube, a mask and mouth tube combination, a trachea tube, a nasal tube, a tent or a small room.

As is clearly shown in FIG. 2, the end 5b of exhalation tube 5 is connected to a fitting which passes through the end of containment case 7 in a sealed fashion and is joined to the inlet of a filter 25 by a connector 26. The filter 25 is similar to filter 13, constituting a standard HME filter. The outlet of filter 25 is connected to a non-collapsible flexible tube 27. Tube 27 terminates in an adapter 28 which passes in sealed fashion through a side wall of the containment case 7, providing an outlet for the filtered exhaled air.

Mounted on filter 25 there is a sensor switch 29. Sensor switch 29 is connected by a tube 30 to a lateral outlet 26a of fitting 26. In similar fashion, the sensor switch 29 is connected by a tube 31 to a lateral outlet 14a of connector 14 attached to filter 13. Tube 31 will contain air at ambient pressure. Tube 30 will contain air at a slightly higher pressure during exhalation by the patient. Sensor switch 29 has an output 29a (see FIG. 4) which becomes part of the sensor output cable 10 of FIG. 1. Sensor switch 29 will send a signal to control unit 8 at the during some portion of each exhalation by the patient. The sensor signal could be sent to the control unit 8 at the initiation of each exhalation. The purpose of this will be apparent hereinafter. The signals from sensor switch 29 also assure that the patient is breathing properly.

In the embodiment described, flexible inhalation tube 4 and flexible exhalation tube 5, as well as Y-adapter 3 and mouth piece 1 should not leak to atmosphere outside containment case 7. With other types of drugs this requirement would be less stringent.

Air pulses from pulsed air line 11 actuate the nebulizer. It will be noted however, that the pulses do not enter the plenum chamber 20. The pulses are electronically controlled by control unit 8. The pulsed air is preferably clean and of the same components and percentages as atmospheric air.

In the exemplary embodiment described, the volume of air required for nebulization ranges from 3.5 to 8.0 liters per minute. The maximum required pressure is about 60 psi. Air pressure will be regulated over the range of from about 20 psi to about 60 psi. The Air pressure will be set upon assembly of the pulmonary dosing system. These parameters may vary depending on the circumstances and the drug being dispensed.

It has been found that it is especially useful for some therapies that the drug aerosol reaches the deep lung. The entire volume of each breath is called the "inspired volume". This inspired volume can be a normal breath, referred to as "tidal volume", or could be a deep breath of much greater volume, referred to as a "vital capacity" breath. With cooperation from the patient (in drawing a deep breath), the device enables this deep penetration by providing that the metered volume of drug aerosol from the plenum forms the first part of each inhaled breath (approximately equal to the tidal volume) and is followed by a volume of air which makes up the latter part of each inhaled breath (the remainder of the vital capacity). It has been determined that this air portion in the latter part of each breath tends to help push the initial drug portion down into the deep lung. If the drug made up most of the entire breath, then the latter part of each breath would not be delivered to the deep lung and may not be available for maximum benefit.

It has been found that an air to drug aerosol volume ratio of at least about 1 to 1 is particularly efficient, meaning that each breath would be ½ drug followed by ½ air. More air is also useful, but at some point the efficiency in terms of the time for completing treatment drops off because very little drug is being administered. We have found that an air to drug aerosol volume ratio of about 2 to 1 is particularly preferred, meaning that each breath would be ⅓ drug followed by ⅔ air. Therefore, the preferred range of air/drug in each inspired volume would be between about 1:1 and 3:1, more preferably between 1:1 and 2:1.

For the more efficient operation, the plenum is provided during the exhalation phase with a drug aerosol volume equal to about ¼ to ½ of the patient's normal inspired volume. This volume is then inhaled in the first part of a breath followed by the air component in the latter part of the breath. The tidal volume and vital capacity may be determined by known pulmonary function tests. The control system is then programmed to deliver the selected amount of drug aerosol to the plenum based on the pulmonary function of the animal or human.

The air supply from line 11 and line 19h to nebulizer 19 will be pulsed in a cycle synchronous with the patient's exhaled breath. Sensor switch 29 (a pressure switch) will sense some part of the exhalation process. The signal from sensor switch 29 will cause a solenoid valve (to be described hereinafter) on the compressed air supply to open to nebulizer 19 for a preset pulse width. In the example described above this sequence will occur at each exhalation.

In some instances it is desirable to provide the drug in a more relaxed manner, providing for one or more exhalations between pulses to the nebulizer. The number of exhalations between air pulses will depend upon the patient, the patient's breathing capacity, and the like. As an example, for a given patient, the control unit may be set for three or more exhalations between air pulses. Under this circumstance, the patient's first breath after a pulse would constitute mostly drug. The patient's second breath would also be mostly air and some residual drug. The third breath would be substantially air. Upon the initiation of the third exhalation, an air pulse would occur. Such a cycle is continuously repeated while the drug is being delivered and this is continued for a set number of breaths.

The total number of breaths required to deliver the drug is calculated. The total dose of drug in the nebulizer 19 should be delivered by the set number of breaths. The control unit 8 (see FIG. 1) is provided with a liquid crystal display 32, visible to the patient, that will count down the number of breaths required to consume the drug dose. Control unit 8 is also provided with a reset button in case the drug is not completely consumed in the allocated number of breaths. Similarly, the control unit is provided with a remote on-off switch 33 enabling the patient or an operator to stop and restart a cycle should the patient feel either distressed or the need for a few more breaths before the next pulse.

It has been found that the effective drug dosage for particular patient may vary. A method for using the inventive device for determination of an effective drug dosage generally includes the steps of (a) administering a tracer material to the patient by inhalation with an inhalation device; (b) determining the amount deposited and optionally the deposition pattern of the tracer material in the patient; (c) calculating from the amount of deposited tracer material, and optionally from the deposition pattern of the tracer material; the number of breaths required from the patient; and (d) administering the antineoplastic drug to the patient with the inhalation device for the calculated number of breaths.

Generally the dosage determination method contemplates the development of data from a test or tests conducted on the patient prior to administering the drug by inhalation. The data include but are not limited to particle or aerosol size and other characteristics, the minimum number of breaths for good distribution, type of breath (e.g. deep or shallow), the pulmonary system distribution and the inhaled amount of a tracer material; apparatus parameters; patient breathing or pulmonary characteristics; and the like. The tracer material typically has deposition characteristics substantially the same as the drug to be administered or the administration of drug is corrected for this difference. In practice having the tracer material have the same aerosol characteristics as the drug is preferred and practical in a real clinical device. Device settings, number of dosing breaths, type of breaths, and so on are typically calculated from the tests.

One preferred method of dosage determination is disclosed in US patent application filed contemporaneously herewith entitled "Method for Safely and Effectively Administering a Drug by Inhalation", and having docket number 22000(3)9901, the disclosure of which is incorporated by reference as if fully rewritten herein.

One of the major problems with inhalational chemotherapy is the delivery of accurate amounts of drug to a patient. It has now been found that the use of tracer materials such as Tc 99 m scintigraphy is a safe and useful tool in controlling and delivering the correct amount and pulmonary distribution of highly toxic antineoplastic drug to be given to patients by inhalation.

Patients who are candidates for inhalational chemotherapy using highly toxic drugs will inhale a quantity of the vehicle that is to be used with the drug. The vehicle will contain a particle having Tc 99 m as a tracer. Following the inhalation, the distribution and quantity of the Tc 99 m in the respiratory tract will be determined by the usual methods (such as with a gamma camera). The information is then used to compute the various settings of an inhalational device, breathing pattern of a patient, and desired amount of toxic drug that will be administered to the patient.

As most easily seen in FIG. 2, an inhalation filter 161 may intercept and capture substantially all of a tracer material, drug or other aerosolized material that is drawn into contact with the filter 161 as the patient inhales during the first filter test phase of the method. Bypass filter 163 captures substantially all of the aerosolized material that bypasses filter 161 and flows toward and into exhalation tube 5. The patient interface is constructed so that the device is sealed and usable with the filters 161, 163 present or removed. When filter 161 is used it is placed so that all air inspired by the patient is filtered and is of a type wherein substantially all aerosol particles are removed so that the patient is not exposed to the aerosolized tracer materials.

There are three main embodiments of the determination of drug dosage. A first embodiment contemplates performing a two step testing procedure for a patient that is determined to have a substantially normal pulmonary system. A second embodiment contemplates performing a three step testing procedure on a patient that is determined to have a substantially impaired pulmonary system. A third embodiment contemplates performing an evaluation of the patient to determine the category "substantially normal or repeat patient" or "substantially impaired or at high risk" into which the particular patient fits followed by the testing procedure for that category. Typically, a substantially normal or repeat patient would be treated with the two step testing procedure and a substantially impaired or high-risk patient would be treated with the three step testing procedure.

Two Step Filter Test Procedure

The two step filter testing procedure contemplates developing dosing information for the individual patient using the following steps. The first step includes a set of filters (inhalation filter 161 and blow-by filter 163) and is called the filter portion of the test. The second step dispenses with at least the inhalation filter and applies a tracer material directly to the pulmonary system of a patient. Both the first filter test and the second filter test, develop information that is used in determining dosing information for treatment of the patient. The patient breathes through the mouthpiece for a set number and type of breath. Typically the breaths contemplated include a set of preparatory breaths numbering from zero to 20 during which no aerosolized tracer material is released by the inhalation device and a dosing breath for which a controlled dose of tracer material is released. The patient then repeats the breathing procedure a predetermined number of times, typically zero to twenty times, more preferably one to ten times. Most preferred is two preparatory breaths followed by a dosing breath, with the breathing procedure repeated a total of five times. A typical breathing sequence that is expected to provide good results for the filter test uses at least one to six preparatory breaths followed by a dosing breath and a breath hold period for each dosing breath. This sequence is repeated from one to six times. The preparatory breaths are typically normal breathing breaths; but may be any found useful for providing good patient compliance and proper dosing during the following dosing breath. The dosing breaths and the following breath-holding period are typically those found to provide predetermined pulmonary deposition and pulmonary distribution. Deposition parameters found for the individual patient using the tests of the present invention may likewise be used in a subsequent test session to properly test and treat the patient. Because of disease progression or other variables present in an individual patient, one or more additional deposition tests may be needed, even with preliminary guidelines from previous deposition studies, in order to properly dose the patient. However, it is contemplated that, except for very severe cases, usually one test will suffice and two tests will almost always be sufficient.

When the patient performs the aforementioned dosing breath, a tracer material is released as an aerosol and administered to the patient. Of course, because of the presence of inhalation filter 161 during the first filter test no tracer material actually reaches the patient but is filtered out and captured on inhalation filter 161. At the same time blow-by tracer materials are captured on blow-by filter 163. Subsequently, the inhalation filter 161 and blow-by filter 163 are removed and tested for the amount of tracer material present. Tracer material testing is a well-known technique and known techniques such as the use of well counters for radioactive materials; detectors for fluorescent materials, color detectors for color, or absorption; and the like are contemplated for the test herein. Specifically preferred is Tc-99 m. Using information including the amount of tracer material nebulized, the amount of tracer material captured on the inhalation filter 161, and the amount of tracer material captured on the by-pass filter 163, radioactive decay times, and the like, the amount and relative percentage of tracer material that is present on the inhalation filter can be determined. The amount of tracer material present on the inhalation filter 161 represents the amount of tracer material that would have been inhaled but for the presence of the inhalation filter 161.

In the second filter test, the foregoing procedure is essentially repeated except that inhalation filter 161 is removed and exhaust filter 25 or an optional replacement blow-by filter (that replaces blow-by filter 163 that was removed for analysis in the first filter test) is used to measure blow-by and exhaled tracer material. The replacement blow-by filter may be dispensed with if a general exhaust filter 25 is used and analyzed, however, a replacement blow-by filter is preferred in order to obtain similar operating conditions. The patient breathes through the mouthpiece as before but for a new set of predetermined number of breaths. Typically the breaths include a set of preparatory breaths (numbering the same as in the first filter test and of the same type) during which no aerosolized tracer material is released by the inhalation device. Following the preparatory breaths, a dosing breath is taken for which a controlled dose of tracer material is released and inhaled followed by the same breath hold period. The patient repeats the preparatory breath and dosing breath-breathing procedure a predetermined number of times, typically five to fifty times, preferably 15 to 40 times and most preferably 20 to 30 times. Most preferred are two preparatory breaths followed by a dosing breath with the sequence repeated twenty-four times. During the second filter test, at each dosing breath a second tracer material is administered to the patient, except this time since filter 161 has been removed and the patient inhales the tracer material. As mentioned above, an optional new by-pass filter that replaces the bypass filter 163 used in the first filter test, or the exhaust filter is now used to measure the amount of blow-by material and the amount of exhaled material from the patient. This allows for correction of the inhaled dose determined in the first filter test to compensate for the amount of material that is inhaled and then exhaled by the patient but never deposited in the pulmonary system. The amount of tracer material actually deposited in the patient and its relative ratio is then determined.

The results of the first filter test and second test are then used to calculate the number of dosing breaths needed, and optionally the corrections to the inhalation device to deliver the predetermined dose to the patient in the subsequent administration step. Corrections to the device, if used, typically include resetting the aerosol generation time, the delay time between activation of the nebulizer and aerosilation, pressure used to drive the nebulizer, amount of drug placed in the device, adjustment of the device to obtain a different particle size, and so on. The patient breathes from the inhalation device used for the tests, or a substantially similar device, for the calculated number of dosage breaths. The number of preparatory breaths between each dosing breath step is typically the same for both filter tests.

Three Step Testing Procedure

The three step testing procedure that is used for patients having substantially impaired pulmonary systems has the identical first two steps as the two-step testing procedure discussed above. A third step provides for taking a scintigraphic image of the patient immediately after the second step. This third step provides information as to the distribution of the aerosolized tracer material in the patient. For radioactive tracers, a radiographic image of the patient is made using common imaging techniques. In making the determinations as to amount of inhaled tracer material present at a site regions of interest are defined in the image. For example, the region of interest may be the whole of both lungs. If Tc-99m has been used as the tracer material then the counts in the lungs are determined using imaging techniques. Next the counts in the kidneys, bladder, and those generally attributable to Tc-99m that has left the lungs are determined and these counts are added to the lung counts. Counts in the mouth, stomach and other areas are not counted toward the lung counts. Since the amount of tracer material that has been aerosolized, lost in the system and captured in the by-pass filters and/or exhaust filter 25 can be determined, the relative amount of tracer material in the lung can be calculated. Decay of radioactive tracer material is corrected by tracking time during the test procedure. Finally, the information obtained in the first and second filter tests is used to correct for attenuation of radioactive material by the patient's body by correlating total body counts during the scintigraphy tests to the amount of material that was inhaled and remained in the patient during the second filter test.

From the information obtained in either the two-step test or the three-step test one can determine the amount of drug to be aerosolized, inhalation device settings needed to obtain the required amount of aerosolized drug to be administered to the patient and the required number of dosage breaths needed to administer the predetermined dose of drug to the patient.

It will be understood by one skilled in the art that the pulse sequence can be manipulated in any number of ways to change the rate of drug delivery over time. For example, the drug quantity can be ramped up or ramped down over time, or otherwise set at whatever quantity versus time is desired.

The amount/timing of drug delivery could also be altered based on feedback data from the patient. Spirometry data (such as tidal volume, vital capacity, inhalation rate, etc.) or physiological data in the exhaled breath (such as residual drug content, blood gases, mass balance) could be monitored to calculate and adjust new delivery profiles. Biosensors (such as EKG, glucose and pulse sensors) could be used to measure body functions or responses to the drug to provide feedback that is used to customize the delivery profile and optimize mass transfer of drug.

It is also to be understood that the amount/timing of drug delivery does not have to be accomplished automatically in the present invention. The drug can be dosed manually, for example by a nurse activating a trigger mechanism, based on the breathing cycle of the patient.

As indicated above, chemotherapy drugs are generally extremely caustic and also may have certain toxic effects. It is therefore imperative that such a drug be contained. Containment of any fugitive aerosolized drug must be assured. This is accomplished by the provision of containment case 7 and by maintaining a negative pressure (vacuum) within the containment case. The lid 7*a* of containment case 7, when closed, makes a seal with the containment case body 7*b*.

Figure 5:
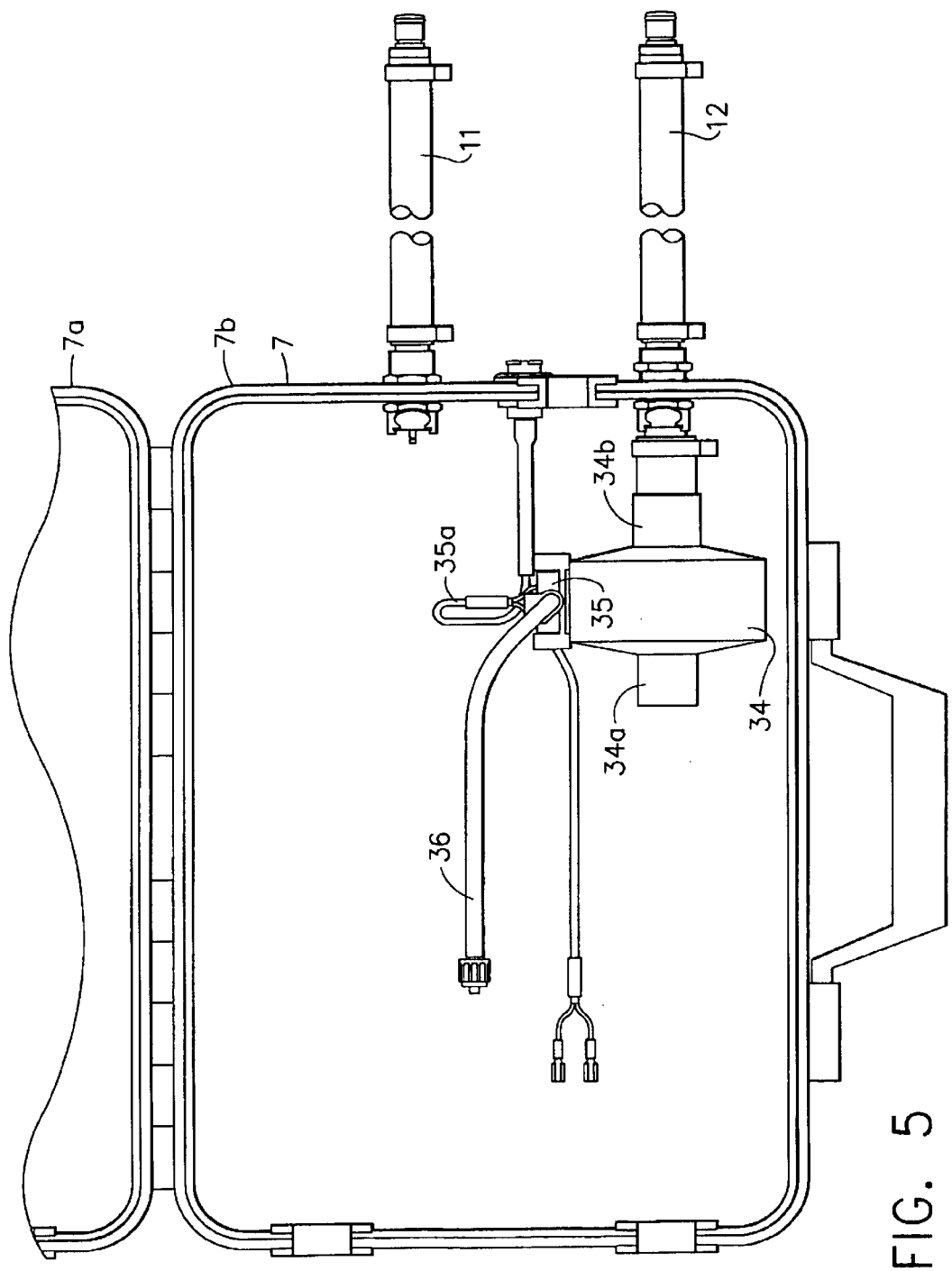
FIG. 5 is a fragmentary plan view illustrating the vacuum components of the present invention located within the containment case.
Figure 6:
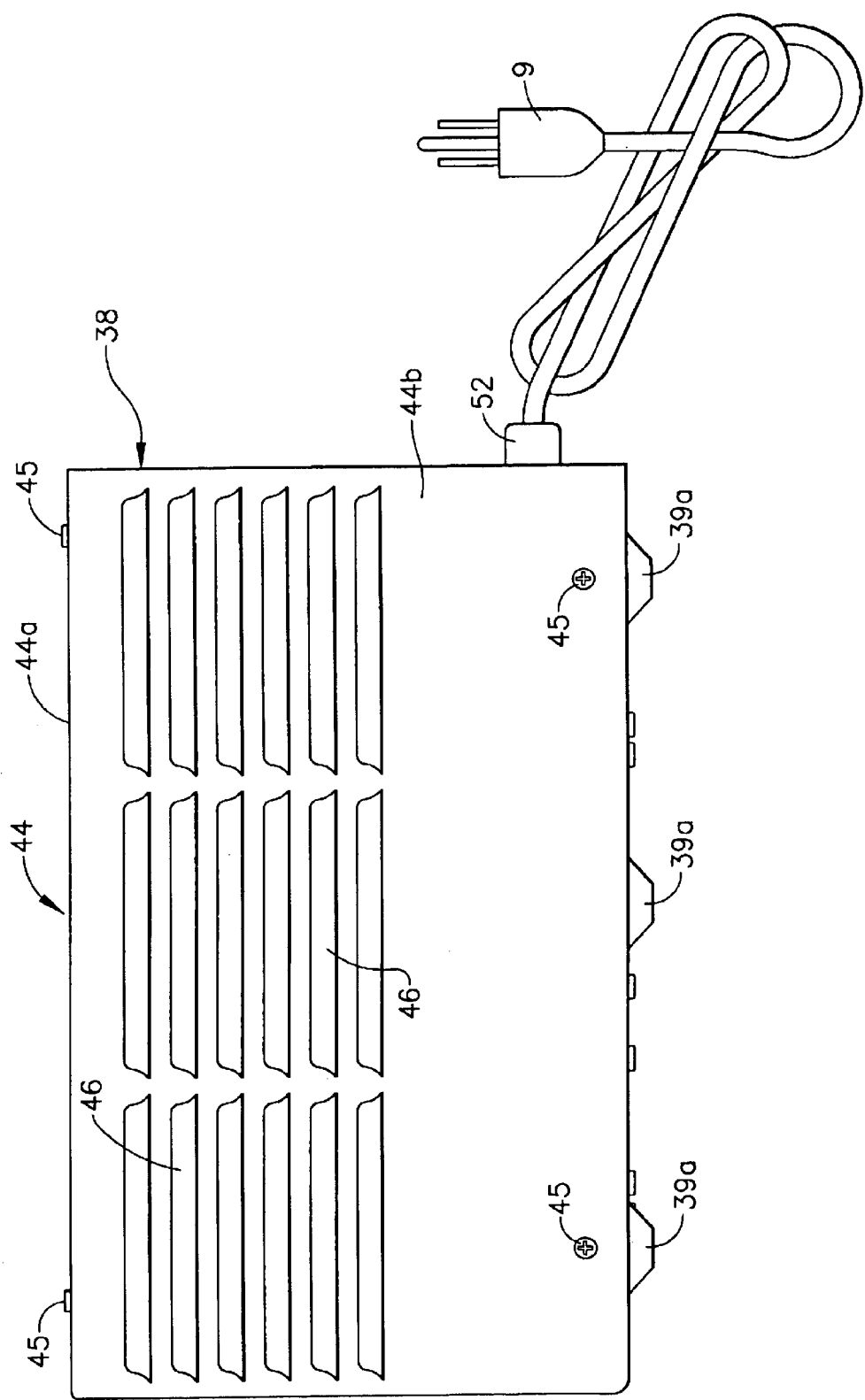
FIG. 6 is a side elevational view of the control assembly of the present invention.
Figure 7:
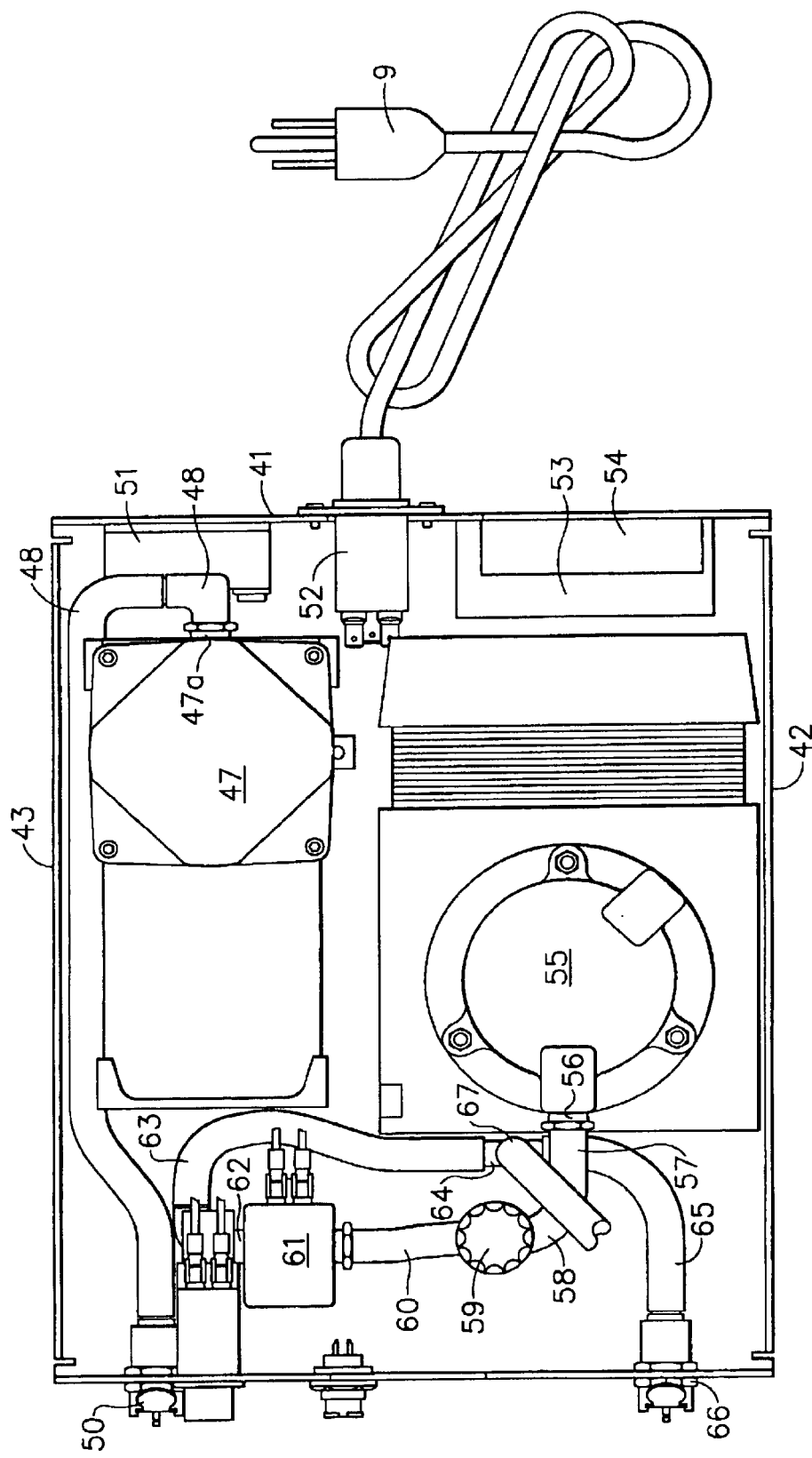
FIG. 7 is a plan view of the control assembly with its outer casing removed, together with the upper layer of the components.
Figure 8:
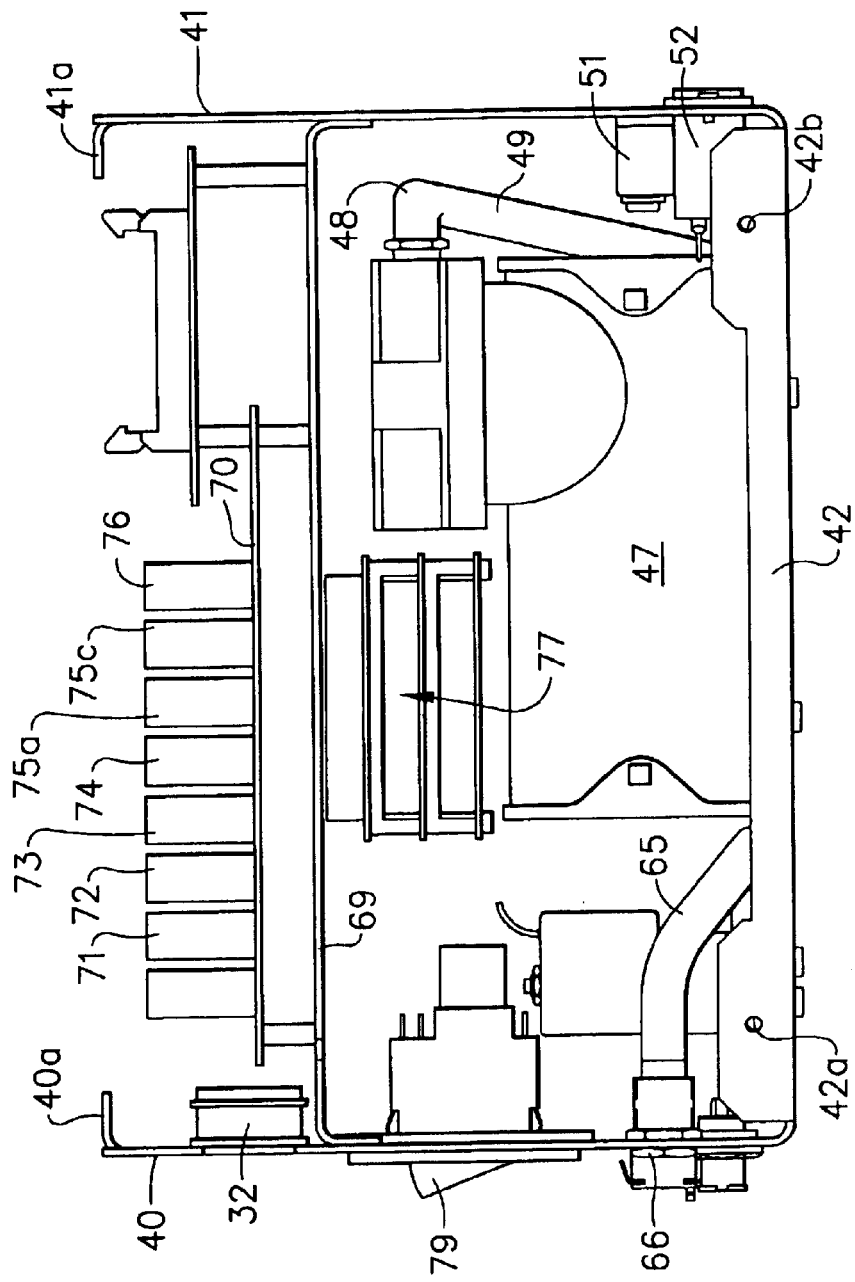
FIG. 8 is a side elevational view of the control assembly with the outer casing and the compressor removed.
Figure 9:
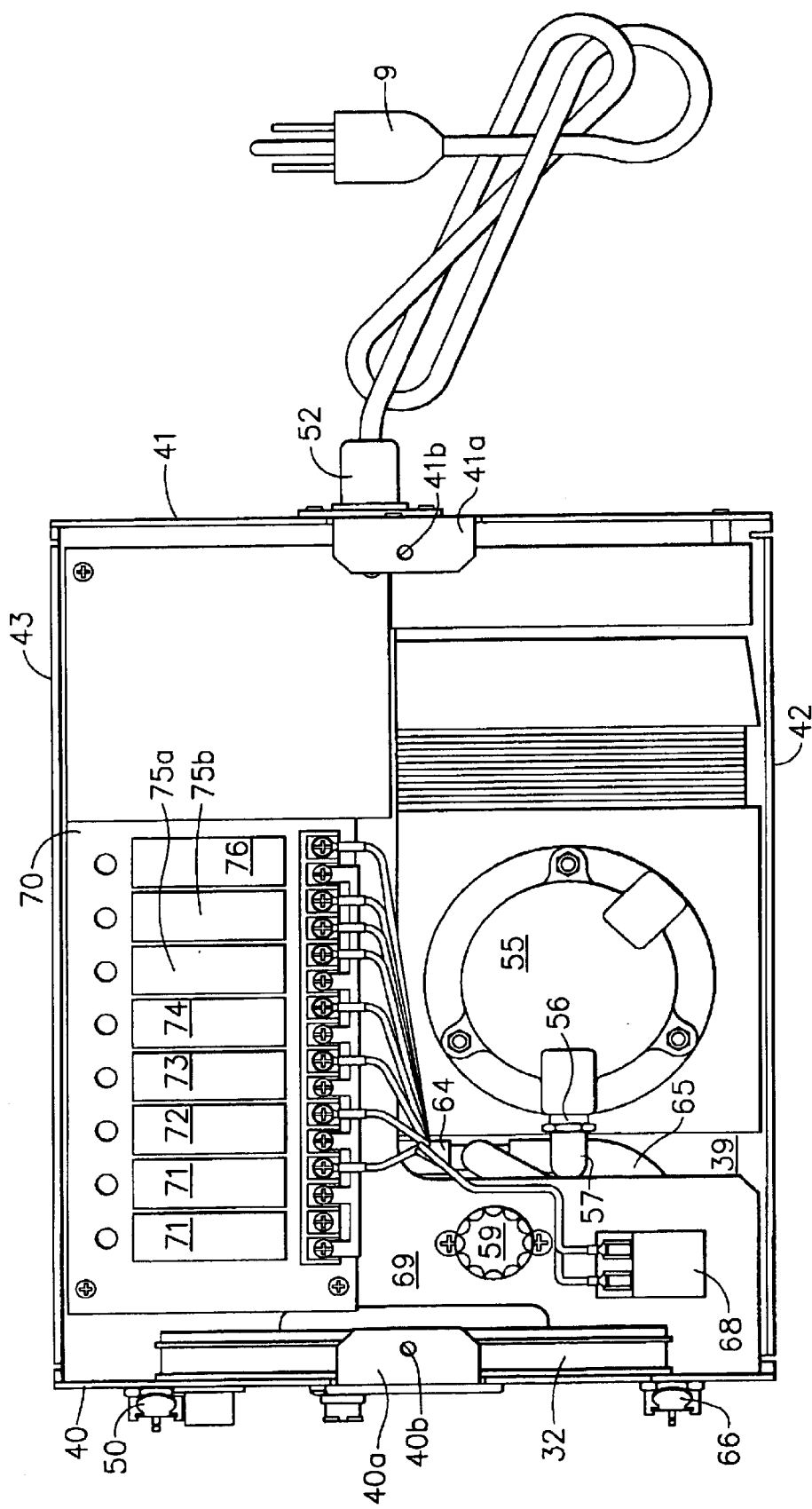
FIG. 9 is a plan view of the control assembly with the outer casing thereof removed.

Reference is now made both to FIGS. 4 and 5. A filter 34, similar to filters 13 and 25, is located within containment case 7. The filter 34 has an inlet 34*a* open to the interior of containment case 7. Filter 34 has an outlet 34*b* provided with an appropriate adapter to enable it to be connected to vacuum line 12, in a sealed fashion through the end wall of containment case 7. Vacuum line 12 is connected to a vacuum pump within control unit 8, as will be explained hereinafter.

Filter 34 has mounted thereon a vacuum sensor switch. The sensor switch 35 is connected by a tube 36 to a lateral outlet 15*a* of elbow connector 15. Sensor switch 35 senses the presence of a vacuum within containment case 7 and has an output 35*a* connected to the sensor output cable 10 (see FIG. 1) to control unit 8. Should there be a loss of vacuum, control unit 8 will turn off the air pulse compressor to the nebulizer.

Filter 13, 25 and 35 are all described as constituting standard HME filters. In fact, these filters could be any devices for removing toxic materials. Absorbers (such as activated charcoal) or physical separators (such as electrostatic precipitators) could be used.

The interior of containment case 7 should be easy to clean. All interior surfaces should be smooth and without crevices. After each use, the entire contents of containment case 7 (except vacuum filter 34 and vacuum sensor 35), together with inhalation tube 4, exhalation tube 5, Y-fitting 3, mouth piece 1 and mask 2 will be disposed of. FIG. 4 illustrates the arrangement of the various elements within the containment case 7. In FIG. 5, everything has been removed from the containment case 7 except for the vacuum filter and vacuum sensor which are partially obscured in FIG. 4.

Reference is now made to FIGS. 1 and 6–9 in which the control unit 8 is illustrated. Control unit 8 has a housing generally indicated at 38. As is best shown in FIGS. 8 and 9, the housing comprises a bottom panel 39 with upturned front and rear end panels 40 and 41, respectively. Bottom panel 39 has, along each of its longitudinal edges, an upstanding flange. These flanges are shown at 42 and 43. Flange 42 is provided near its ends with threaded perforations 42*a* and 42*b*. Longitudinal flange 43 will be provided with similar threaded perforations (not shown). Front panel 40 has along its upper edge an integral in-turned tab 40*a*. The tab 40*a* has a threaded perforation 40*b* formed therethrough (see FIGS. 7 and 9). In a similar fashion, the rear panel 41 is provided with an in-turned tab 41*a*, centered with respect to its upper edge. The tab 41*a* has a threaded perforation 41*b* extending therethrough. The housing 38 is completed by a U-shaped outer casing generally indicated at 44 and comprising the top 44*a* and sides 44*b* and 44*c* of control unit 8. As is shown in FIGS. 1 and 6, the side 44*b* of control unit 8 is attached to the longitudinal flange 42 by means of screws 45 threadedly engaged in flange perforations 42*a* and 42*b* (see FIG. 8). It is within the scope of the invention to provide side 44*b* with a plurality of louvers to allow for cooling of the contents of housing 38. Side wall 44*c* may be identical to side wall 44*b* and may be attached to longitudinal flange 43 (see FIG. 7) in an identical manner. The top 44*a* is attached to in-turned flanges 40*a* and 41*a* of the front and rear panels, respectively by means of additional screws 45, as shown in FIGS. 1 and 6. The bottom panel is provided with depressions 39*a* serving as feet for the control unit 8, and allowing air circulation around the control unit.

Reference is made to FIGS. 7 and 8 which illustrate a vacuum pump 47. Vacuum pump 47 has an outlet 47*a* to which an elbow hose barb 48 is connected. Hose 49 is connected to elbow 48 and extends to the forward panel 40 of control unit 8, where it is attached to a vacuum connector 50 which extends through front panel 40. Vacuum connector 50 is adapted to receive the free end of vacuum hose 12. As is shown in FIG. 7, immediately behind vacuum pump 47 there is a solid state relay 51 which turns the vacuum pump 47 on and off in a response to a signal from the computer (to be described hereinafter).

Centered on the back panel 41, near its bottom edge, there is a connector 52 for power cord 9. Elements 53 and 54, adjacent rear wall 41 constitute 12 V and 5 V DC power supplies.

To supply the pulsed air for nebulizer 19, control unit 8 contains a compressor. While the compressor has been removed from FIG. 8 so that other elements could be seen, it is shown in FIGS. 7 and 9 at 55. The compressor 55 has an outlet 56 which is connected by means of an elbow fitting 57 to a tube 58. As is shown in FIG. 7, tube 58 is connected to a pressure regulator 59. Regulator 59, in turn, is connected by a tube 60 to the inlet of a pulse generating electric air valve 61. The outlet of the pulse generating electric air valve is provided with an elbow 62, connected to a tube 63. Tube 63 is connected to one port of a T-fitting 64. Another port of T-fitting 64 is connected by tube 65 to a fitting 66 which extends through front panel 40 of control unit 8. Pulsed air line 11 attaches to fitting 66 (see FIG. 1). The intermediate port of T-fitting 64 is connected by a tube 67 to a pressure sensing safety switch 68. Safety switch 68 assures proper pressure from compressor 55. It will also cause the compressor to be shut down should there be a gross hose or fitting leak.

Turning to FIGS. 8 and 9, the front and rear ends 40 and 41, support an L-shaped shelf 69. Mounted on shelf 69 there is an 8-position single channel I/O board 70. The board 70 serves as an interface between the computer (to be described) and various sensors of the pulmonary dosing system. Attached to the I/O board 70, there are a number of DC input modules 71–74. There are also DC output modules 75*a* and 75*b*, together with an AC output module 76.

Just below shelf 69 there is a module generally indicated at 77 which comprises an embedded computer, a keypad and LCD interface board, and a signal conditioning interface.

Turning to FIG. 1, the forward face of control unit 8 has the liquid crystal display 32, mentioned above. In addition, there is a keypad 78 providing an interface between the operator and the computer. The overall control unit has a main on/off switch 79 and the vacuum connection 50, the pulsed air connection 66, the remote switch connection 80 to receive the connector end of manual switch 33 by which the patient or operator can introduce a pause in the dosing cycle. Finally, the control unit has a connector 10a for sensor cable 10 which contains the outputs of exhalation sensor switch 29 (see FIG. 2) and vacuum sensor switch 35.

The use of compressor 55 to provide the pulsed air for nebulizer 19 is preferred, because it renders the overall pulmonary dosing system a self-contained system. There is no need to provide an air tank, or to rely on air supplied by a hospital or the like.

From the above description it will be noted that the control 8 has three operator or patient interfaces, each passing information in only one direction. The liquid crystal display 32 constitutes a user interface and will allow the control system to communicate with the operator and the patient, prompting the operator for inputs and conveying information to the patient or the operator during operation of the pulmonary dosing system. Keypad 78 is an operator interface and allows the operator to enter numeric data into the system. Furthermore, the keypad will enable the operator to enter system commands (such as START, PAUSE/STOP, and RESET) by means of dedicated keys on the keypad. Keypad 78 will also have an enter key enabling the operator to instruct the control unit 8 to accept data entered by means of the keypad.

Remote switch 33 is used to indicate when to start or pause the operation of the pulmonary dosing system. Control unit 8 is provided with a built-in beeper or alarm which is sounded every time the remote switch is actuated. The remote switch may be actuated by either a qualified operator or the patient. A trained operator should be present at all times during operation of the pulmonary dosing system. It is not to be operated in an unattended mode. Since, in the embodiment described, the drugs being delivered by the pulmonary dosing system are highly toxic, both the system and its software are designed and constructed to minimize the safety hazard posed by the drugs. It will be assumed that the pulmonary dosing system will be powered down any time drugs are loaded into the nebulizer 19, or the lid 7a of containment box 7 is open. In the embodiment described, the patient and the pulmonary delivery system must be enclosed in a negative pressure tent with a HEPA filter as a secondary system to contain aerosolized drug in the event that the patient coughs or removes the mouthpiece prior to exhaling. The operator should not press on/off switch 79 or remote switch 33 unless the patient has the mouthpiece in place in his mouth.

It will be understood that with respect to hardware interfaces, the system will have a dedicated interface to keypad 78, a dedicated interface to liquid crystal display 32, a dedicated interface to the beeper or alarm, and a discrete input/output interface to the rest of the control unit elements. This interface is used by the computer to actuate the mechanical components of the pulmonary delivery system.

The software for controller 77 will perform the following functions: it will allow the operator to set up the system for a particular patient and the hardware being used; it will notify the operator when any of the exception modes (pause, reset, or set up mode) are detected; it will operate the system in a consistent manner; and it will notify the operator when any of the alarm conditions (loss of breath, loss of vacuum, loss air pressure, no breath, long breath, vacuum sensor switch closed, and pressure sensor switch closed) is detected. It will allow the operator to set the time of nebulizer air pulse width, based upon the drug being delivered. It will allow the operator to set the amount of exhales between air pulses based upon the patient to whom the drug is being delivered. When the air compressor has been turned off, the software will see that the vacuum pump will be left on, to assure complete evacuation of any aerosolized drug. When a loss of vacuum is detected, the software will cause the air compressor 55 to be shut down while the vacuum pump continues to run until power is turned off. The software enables the operator to enter the dose either in terms of milliliters or number of breaths. The software will calculate the number of breaths required to empty the nebulizer 19. The software will also cause the beeper or alarm to sound if sensor 29 does not detect any breaths for 10 seconds. This will assure that the patient is breathing properly and that the patient is exhaling into the mouthpiece. The beeper or alarm will sound if there is a loss of air pressure as detected by pressure sensor switch 68, or if there is a loss of vacuum as sensed by vacuum sensor switch 35. The software also provides a number of other checks, as will be apparent hereinafter. For example, the pulmonary delivery system will not be allowed to start a cycle if the remote switch 33 is not plugged into connector 80.

Again, it is to be emphasized that in addition to the automatic dosing described herein, the present invention also encompasses manual dosing of the drug, for example by a nurse or technician activating a trigger mechanism, based on the breathing cycle of the patient.

The software operating requirements for the pulmonary delivery system may be subdivided into a number of categories.

Pre-drug Delivery Phase

This category relates to operating requirements prior to drug delivery. These requirements are in an expected sequence. Only the sequence in which the operator enters various parameters noted below can be changed without affecting the overall expected operation.

When power is applied to the system, the software will initialize the system and perform self-checks of the electronic components. Air valve 61 to which the output of compressor 55 is attached via pressure regulator 59 is vented to atmosphere. Compressor 55 is initialized to be off. After the system powers up, the software detects that the remote switch 23 is properly connected. If not, the software will not allow a cycle to start. Thereafter, the vacuum pump is turned on and the software checks to see that vacuum sensor switch 35 is closed, indicating that a vacuum is present in containment case 7. The vacuum sensor switch 35 must close within 5 seconds of the vacuum being turned on or the software will not allow a cycle to start.

Next, the operator is prompted by liquid crystal display 32 to enter the specific delivery cycle parameters (drug dosage, air pulse width, and a number of breaths between air pulses). In the exemplary embodiment of the pulmonary dosing system, the acceptable dosage ranged from 0.5 ml to 5.0 ml with an increment of 0.5 ml and a default of 0 ml. The operator cannot proceed unless a dosage value in the acceptable range has been entered. Next, the operator must enter the air pulse width which, in the exemplary embodiment, has an acceptable range of 1 sec to 10 sec with an acceptable increment of 1 sec and a default of 0 sec. Again, the operator cannot proceed further until an air pulse width value within the acceptable range has been entered. Finally, the operator must enter the number of exhales between air pulses. The exemplary embodiment has an acceptable range of from 1 exhale to 10 exhales with an increment of 1 exhale and a default of 0. Nothing further can be done until the operator enters an input within the acceptable range. Once all of the inputs have been entered and have been determined to be valid, the software looks for actuation of on/off switch 79 or remote switch 33. When a signal is received from either of these switches, the software will transition to the drug delivery phase of the operation.

Drug Delivery Phase

At the beginning of the drug delivery phase, air compressor 55 is turned on and remains on throughout this phase. The software will allow three seconds for the air compressor to come up to pressure, as indicated by pressure sensor safety switch 68. The software calculates the total number of breaths required by the user to consume the dosage entered by the operator. The total number of breaths comprises the number of breaths equivalent to the entered dose, plus the number of breaths between air pulses. The number of breaths equivalent to a full dose depends upon drug formulation and the nebulizer (or other apparatus for providing a pulsed amount of respirable drug) used, and the patient, himself. The total number of breaths will be displayed to the user by the liquid crystal display 32. The total will be diminished by 1 each time the system detects a breath. The software considers a breath to be detected when the exhale sensor switch 29 (a pressure sensor switch) closes its contacts and then opens its contacts. Contacts will remain closed for no more than 10 seconds, and if they remain closed for longer than 10 seconds, the beeper or alarm will be sounded, the compressor 55 will be turned off and the delivery cycle will be aborted. The drug delivery will start by opening the pulse generating electric air valve 61 the required number of seconds after an exhale has been detected by sensor switch 29 and the sensor switch contacts open. The software will then count the required number of breaths before the next air pulse is delivered to the nebulizer 19. Every time the pulse generating electric air valve 61 is opened, to deliver a pulse to the nebulizer 19, the software checks the pressure sensor switch 68. The pressure sensor switch 68 closes and remains closed until the pulse generating electric air valve 61 shifts to divert air to atmosphere. The pressure sensor switch 68 will open in no more than three seconds after the pulse generating electric air valve 61 closes. If this does not happen, the beeper or alarm is sounded, the air compressor 55 is turned off, and the delivery cycle is aborted. When the liquid crystal display 32 indicates that the number of breaths is 0, the software turns off compressor 55, ending the drug delivery phase. The system will then advance to the post-drug delivery phase.

Post-Drug Delivery Phase

In this phase, the software keeps vacuum pump 47 running for a specified amount of time after drug delivery ceases. The operator sets this time period when the system is initially configured. At the end of this specified time, the vacuum pump 47 will be turned off by the software. When the vacuum pump is turned off, the liquid crystal display 32 will prompt the operator to power down the system.

General Safety Requirements

The software continuously monitors the vacuum sensor switch 29. Should the vacuum fail, software will cause the beeper or alarm to sound, the current cycle to be aborted and the air compressor to be turned off.

Exception Modes

There are three exception modes (pause mode, reset mode, and setup mode). These modes come into play only to handle abnormal conditions. The pause mode is entered only from the drug delivery phase of the system. The purpose of the pause mode is to give the patient a brief respite to allow the patient to re-compose himself. A typical example would be if the patient starts to cough. The pause mode can be initiated by pressing on/off switch 79 on front panel 40 or by pressing the remote switch 33. In the pause mode, the software suspends air pulsing. The count in terms of number of breaths remains and the number of breaths to the next air pulse are saved so that the system can resume normal operation when it exits from this mode. The no breath alarm (described hereinafter) is disabled in this mode. The pause mode can be terminated by again pressing either the on/off button 79 or the remote switch 33. If the system is in the pause mode for 10 minutes, the air compressor will be turned off and the operator will be required to power down the system.

The reset mode allows the operator to run the system with no drugs so that the patient can become comfortable with the procedure. This mode also allows the operator to restart the system when appropriate. The reset mode is entered either from the drug delivery phase or the post-drug delivery phase. The software will shut down the compressor when the mode is entered. All of the cycle parameters entered by the operator will be reset to 0. The no breath alarm is cleared. It should be noted that the system cannot be reset from any other alarm condition. The above conditions having been met, the system will exit the reset mode and re-enter the pre-drug delivery phase.

The setup mode allows the system to be configured for a particular nebulizer and/or clinical trial. Only trained and authorized personnel will set these parameters. The only times these parameters are expected to change, after having been initially set, is if the nebulizer changes. This mode can only be entered by use of appropriate keys while power is applied to the system. Once the system has powered up, the user is locked out of the setup mode. Once the setup mode is recognized by the software, the software must initialize the system and perform self-checks of the electronic hardware, initialize the compressor, check for the presence of the remote switch 33 and check the vacuum pump 47 and vacuum sensor switch 29.

Once in the setup mode, the software will prompt the user to enter the values for the parameters listed below. The software will display the current value of the parameters. If the user desires to retain this value, he simply presses the enter key. Otherwise, the user enters the desired value using the keypad. When the user enters a parameter (by pressing the enter key), the software will display the value that will be stored in non-volatile memory. If the value entered by the user is larger than the maximum value, or less than the minimum value, the actual maximum or minimum value will be displayed. To confirm the entry, the user must press the enter key a second time. Once this has been done, the parameters will be loaded into memory. To change the entry, the user presses the appropriate numbers on the keypad. The user will be able to delete the last number by pressing the pound key ("#") on the keypad. This key functions like a backspace key on a normal computer keyboard. The parameters mentioned above are as follows. The number of breaths per full dose has an acceptable range of from 10 breaths to 999 breaths with an increment of one breath and a default value of 100 breaths. The time after the dose is delivered has an acceptable range of 0.5 to 10 minutes with an increment of 0.5 minutes and a default of 1 minute. The maximum time the exhale switch is closed has an acceptable range of 1 to 30 seconds with an increment of 1 second and a default of 10 seconds. The maximum time between breaths has an acceptable range of 1 to 60 seconds with an increment of 1 second and a default of 20 seconds. Once a parameter has been entered, the software will ask the operator if he desires to exit the setup mode or to enter the next parameter. If the operator desires to exit the setup mode, the operator has the option of entering the pre-drug delivery phase of the system, or to shut down the system.

Alarms

The following is a list of abnormal conditions detectable by the software. In all cases, the owner is notified of the alarm condition by the controller. One abnormal condition is the loss of vacuum. If a loss of vacuum is detected, the user must shut down the system. Once the power is removed from the system, the operator will open the containment case 7 and determine the cause of the leak and correct it. If this occurs, drug delivery by the system can start. Software defines a loss of vacuum when the contacts of vacuum sensor switch 29 remain open for more than 1 second when the software expects a vacuum to be present in the containment case 7. When the software detects a loss of vacuum, it will abort the current cycle and turn off the air compressor (if appropriate). When the air compressor is turned off, the vacuum pump will keep running. The pulse generating electric air valve will vent the compressor air to atmosphere. The loss of vacuum will cause the beeper or alarm to sound three times. When a loss of vacuum is detected, the liquid crystal display 32 will display the message "LOSS OF VACUUM, SHUTDOWN SYSTEM". When a loss of vacuum is detected, the operator's only option is to shutdown (remove power from) the system.

Another abnormal condition is a loss of pressure and the operator will be required to shutdown the system. The operator will open the containment case 7 or the control unit 8, determine the cause and correct the pressure leak. Thereafter, the drug delivery by the pulmonary delivery system can start. The software defines a loss of pressure if the contacts of pressure sensor safety switch 68 remain open for at least 0.5 seconds after the software expects them to close. Whenever a loss of pressure is detected, the software will abort the current cycle. The compressor 55 will be shutdown and the vacuum pump 47 will be kept running. The pulse generating electric air valve will vent the compressor air to atmosphere and the beeper or alarm will be sounded three times. The liquid crystal display 32 will show the message "LOSS OF PRESSURE, SHUTDOWN SYSTEM". Again, when a loss of pressure is detected, the only option available to the user is to shutdown (remove power from) the system.

Yet another abnormal condition is a no breath condition which would occur if the patient removes the mouthpiece from his mouth during delivery of the drug. In the no breath mode, the system can pause and wait for the patient to compose himself before resuming delivery of the drug. The software defines a no breath condition if contact closure on the exhale sensor switch 29 is not detected for a time duration specified by the system parameter "MAXIMUM TIME BETWEEN BREATHS". The exhale sensor switch 29 is considered to be closed when the contacts are shorted together for at least one second. A no breath condition will cause the beeper or alarm to sound three times. The liquid crystal display 32 will give the message "UNABLE TO DETECT BREATH, PRESS PAUSE BUTTON TO CONTINUE". If the no breath condition is detected, the control system will enter the pause mode.

Long Breath

If a long breath condition is detected, the operator will be required to shut down the system. This condition can result from a cabling problem or a switch failure. Since the system uses the breath count to determine when the entire drug dose has been supplied to the patient, the problem must be identified and corrected before continuing the operation. The software defines a long breath condition as an instance where the exhale switch contacts remain closed for a period of time defined by the system parameter "MAXIMUM TIME EXHALE SWITCH CLOSED". This condition will cause the current cycle to be aborted. The air compressor is shut down and the vacuum pump is kept running. The pulse generating electric air valve vents the compressor air to atmosphere. Attention will be called to the condition by sounding the beeper or alarm three times. The liquid crystal display 32 will show the message "LONG BREATH, SHUTDOWN SYSTEM". Upon detection of the long breath condition, the operator shall have only the option to shutdown (remove power from) the system.

Vacuum Switch Closed

Vacuum switch closed is another abnormal condition which can only be checked during the power up sequence before the vacuum pump is started or after the pump is turned off. This condition would most likely be due to a problem with the vacuum switch 29 or the wiring between control unit 8 and containment case 7. If a vacuum switch closed condition is detected, the current cycle is aborted. Such a condition is indicated by sounding the beeper or alarm three times, and the liquid crystal display 32 will show the message "VACUUM SWITCH FAILURE, SHUTDOWN SYSTEM". Under this condition, it is again true that the only option open to the operator is to shutdown (remove power from) the system.

Pressure Switch Closed

If the pressure switch closed condition is detected, the operator is required to shutdown the system. This can result from a cabling problem or a switch failure. This is a particular problem because the system needs to be certain that the air pulse is finished. If the air pulse does not complete its cycle properly (air stuck on), this could result in drug leakage into the contamination tent, if not inhaled by the patient. The software defines a pressure switch closed condition if the pressure switch contacts are determined to be closed when the software expects them to be open, pressure switch 68 should be open before starting an air pulse, or at least two seconds after the end of an air pulse. A pressure switch closed condition will cause the current cycle to be aborted, the air compressor 55 is shutdown and the vacuum pump is kept running. The pulse generating electric air valve 61 will vent the compressor air to atmosphere. This condition will be indicated by actuation of the beeper or alarm three times. The liquid crystal display 32 will provide the message "PRESSURE SWITCH FAILURE, SHUTDOWN SYSTEM". In the event of a pressure switch closed condition, the user's only option is to shutdown (remove power from) the system.

The pulmonary dosing system having been described in detail, together with its sequence of operation and the various abnormal conditions it will detect, it will be evident that a pulmonary dosing system capable of safely administering chemotherapy drugs (as well as other drugs) is provided. The pulmonary dosing system is totally self-contained, requiring only connection to a source of electrical current. Certain parameters can be input by a skilled operator, so that the system can be tailored to a particular patient and the particular drug being administered.

Modifications may be made in the invention without departing from the spirit of it. For example, the present invention may be used in veterinary applications. Under these circumstances the patient interface or mask and the dosage delivery software would be customized.

The inlet and exhalation tubes to the mask could be concentric (coaxial). The compressor and vacuum elements could be merged into one pump and a closed system could be provided in this manner. The compressor side provides the pulsed drug to the patient. The vacuum side retrieves the drug and air from the container (as currently shown) and provides it to the compressor side. Of course, the drug is filtered out of the air as it is retrieved and recycled back to the compressor.

The containment case 7 and the control unit 8 could be joined together in one unit. However, seals would still have to be maintained to keep them chemically separate to prevent the drug and gases from getting to the control side of the package. This might be part of an effort to reduce the size of the overall package.

With respect to the plenum, more than one drug could be introduced therein at the same time. The plenum could have an adjustable volume (using a bellows or piston, for example) to allow optimized delivery for different patients and different therapies. It would be possible to substitute for the plenum a control system that would control the timing and velocity of the drug pulse to match the inspired air timing and velocity.

Finally, there are a variety of known electronic solutions for controlling a system like the drug delivery device of the present invention. Any electronically operated device will do. It could easily be controlled by a microprocessor. Other possible features of a controller for the present invention could include:

Sharing data with other devices (such as other diagnostic devices or patient databases) so that information may come from other sources than the front panel entry;

Having lockouts or other security features to control access;

Containing a modem for remote monitoring or reporting;

Being programmable to make it drug specific so that only one drug can be used (identified by bar coding or ion sensing, for example) or patient specific so that positive patient identification is required; and Being programmed to make the modifications based on feedback from sensors, as discussed above.

What is claimed:

1. A pulmonary dosing system for supplying to a patient capable of normal breathing without mechanical assistance a predetermined amount of respirable therapeutically active material, said system comprising a patient interface connected to a flexible inhalation tube and a flexible exhalation tube; a check valve provided in association with said exhalation tube to prevent inhalation therethrough; a first filter having an inlet and an outlet; said exhalation tube being connected to said inlet of said first filter; said outlet of said first filter being in fluid communication with the atmosphere; an apparatus for providing pulsed amounts of said therapeutically active material aerosolized in filtered atmospheric air; said inhalation tube being connected to said apparatus; and a means for pulsing air to entrain said therapeutically active material in a cycle which is triggered by and is synchronous with said patient's unassisted exhalations, for inhalation in conjunction with patient's natural breathing; said pulmonary dosing system designed solely for use independent of a respirator or ventilator.

2. The pulmonary dosing system claimed in claim 1 wherein said respirable therapeutically active material comprises a single respirable drug or a mixture of at least two respirable drugs.

3. The pulmonary dosing system claimed in claim 1 wherein said active material comprises at least one toxic drug.

4. The pulmonary dosing system claimed in claim 1 wherein said patient is chosen from the class consisting of a human patient and an animal patient.

5. The pulmonary dosing system claimed in claim 1 wherein said patient interface is chosen from the class consisting of a mouthpiece, a mask, a combined mask and mouthpiece, a trachea tube, a nasal tube, a tent and a small room.

6. The pulmonary dosing system claimed in claim 1 wherein said patient interface comprises a mask covering the patient's mouth and nose area, a mouthpiece located within said mask and extending therethrough in sealed fashion, said mouthpiece being operatively connected to said inhalation tube and said exhalation tube, said mask also having a connection therein and therethrough to a filter to capture any therapeutically active material should the patient cough.

7. The pulmonary dosing system claimed in claim 1 which does not include a connection for hookup with a respirator or ventilator.

8. The pulmonary dosing system claimed in claim 1 wherein said pulsing means permits at least one exhalation between air pulses.

9. The pulmonary dosing system claimed in claim 8 wherein said respirable therapeutically active material comprises at least one toxic drug.

10. The pulmonary dosing system claimed in claim 1 wherein the inspired volume of each breath has an air to drug aerosol volume ratio of from about 1:1 to about 3:1.

11. The pulmonary dosing system claimed in claim 10 wherein the inspired volume of each breath has an air to drug aerosol ratio of from about 1:1 to about 2:1.

12. A pulmonary dosing system for supplying to a patient capable of normal breathing without mechanical assistance a predetermined amount of respirable therapeutically active material, said system comprising a patient interface connected to a flexible inhalation tube and a flexible exhalation tube; a check valve provided in association with said exhalation tube to prevent inhalation therethrough; a first filter having an inlet and an outlet; said exhalation tube being connected to said inlet of said first filter; said outlet of said first filter being in fluid communication with the atmosphere; an apparatus for providing pulsed amounts of said therapeutically active material aerosolized in filtered atmospheric air; said inhalation tube being connected to said apparatus; and a control unit for pulsing air to entrain said therapeutically active material in a cycle which is triggered by and is synchronous with said patient's unassisted exhalations, for inhalation in conjunction with patient's natural breathing; said pulmonary dosing system designed solely for use independent of a respirator or ventilator.

13. The pulmonary dosing system claimed in claim 12 wherein said respirable therapeutically active material comprises a single respirable drug or a mixture of at least two respirable drugs.

14. The pulmonary dosing system claimed in claim 12 wherein said active material comprises at least one toxic drug.

15. The pulmonary dosing system claimed in claim 12 wherein said patient is chosen from the class consisting of a human patient and an animal patient.

16. The pulmonary dosing system claimed in claim 12 wherein said patient interface is chosen from the class consisting of a mouthpiece, a mask, a combined mask and mouthpiece, a trachea tube, a nasal tube, a tent and a small room.

17. The pulmonary dosing system claimed in claim 12 wherein said patient interface comprises a mask covering the patient's mouth and nose area, a mouthpiece located within said mask and extending therethrough in sealed fashion, said mouthpiece being operatively connected to said inhalation tube and said exhalation tube, said mask also having a connection therein and therethrough to a filter to capture any therapeutically active material should the patient cough.

18. The pulmonary dosing system claimed in claim 12 wherein the inspired volume of each breath has an air to drug aerosol volume ratio of from about 1:1 to about 3:1.

19. The pulmonary dosing system claimed in claim 12 wherein said control unit is programmed to initiate an air pulse during each patient exhalation.

20. The pulmonary dosing system claimed in claim 12 wherein said control unit is programmed to provide air pulses such that there is at least one exhalation of said patient between consecutive air pulses.

21. The pulmonary dosing system claimed in claim 12 wherein said control unit comprises a housing containing a compressor, said compressor having an outlet connected to a pressure regulator, said pressure regulator being connected to a pulse generating valve, said pulse generating valve being connected to a pressure sensing safety switch and to said apparatus for providing pulsed amounts of aerosolizable drug, said housing containing a vacuum pump connected to a filter to provide said negative pressure in containment case holding said pulmonary dosing system, computer having on and off outputs to said compressor and said vacuum pump, said computer having inputs from said pressure sensor, a keypad comprising an interface between said operator and said computer, and comprises the means by which the operator sets the number of patient exhales between pulses and the pulse duration, a liquid crystal display comprising an interface between said computer and said operator and patient, a remote on/pause switch comprising an operator/patient interface with said computer, said computer being configured to control said pulmonary dosing unit within the parameters input by said operator.

22. The pulmonary dosing system claimed in claim 12 wherein said apparatus for providing pulsed amounts of aerosolized material permits at least one exhaltation between air pulses.

23. The pulmonary dosing system according to claim 12 wherein said therapeutically active material comprises at least one toxic drug.

24. The pulmonary dosing system claimed in claims 12 wherein said apparatus for providing pulsed amounts of said therapeutically active material comprises a plenum for holding said material in aerosolized form for inhalation by a patient, an aerosol producing device for delivering aerosolized material to said plenum, a control unit for signaling said aerosol producing device to deliver a selected volume of said aerosolized material to said plenum, said delivered aerosolized material comprising the first part of the inspired volume of the patient's inhalation following said pulse, a source of air for delivering a volume of air making up the latter part of said inspired volume, whereby said air helps to force said volume of aerosolized material deep into the patient's lungs.

25. The pulmonary dosing system claimed in claim 24 wherein the inspired volume of the first breath after an air pulse has an air to drug aerosol ratio of from about 1:1 to about 3:1.

26. The pulmonary dosing system claimed in claim 24 wherein the inspired volume of each breath has an air to drug aerosol volume ratio of from about 1:1 to about 3:1.

27. The pulmonary dosing system claimed in claim 26 wherein the inspired volume of each breath has an air to drug aerosol ratio of from about 1:1 to about 2:1.

28. A pulmonary dosing system for delivering a drug to the lungs of a patient wherein the patient is capable of breathing without mechanical assistance and has an established unassisted breathing cycle comprising an inhalation phase during which a normal inspired volume of gas is inhaled and an exhalation phase during which a normal volume of gas is exhaled, said system comprising a plenum for holding aerosolized drug for inhalation as the first part of the inspired volume of gas for the inhalation phase; an aerosol-producing device for delivering aerosolized drug to the plenum; a controller for signaling the aerosol-producing device to deliver a selected volume of drug aerosol to the plenum prior to the inhalation phase of the patient; a source of air for delivering a volume of air which makes up the latter part of the inspired volume of gas for the inhalation phase; and a patient interface for delivering the selected volume of drug aerosol from the plenum and the volume of air to the patient whereby the selected volume of drug aerosol makes up the first part of the inspired volume of gas and the volume of air makes up the latter part of the inspired volume of gas for unassisted inhalation by the patient into the lungs in conjunction with the patient's natural breathing; said pulmonary dosing system designed solely for use independent of a respirator or ventilator.

29. The pulmonary dosing system claimed in claim 28 wherein said control unit is programmed to initiate an air pulse during each patient exhalation.

30. The pulmonary dosing system claimed in claim 28 wherein said control unit is programmed to provide air pulses such that there is at least one exhalation of said patient between consecutive air pulses.

31. The pulmonary dosing system claimed in claim 28 wherein the inspired volume of the first breath after an air pulse has an air to drug aerosol ratio of from about 1:1 to about 3:1.

32. The pulmonary dosing system claimed in claim 31 wherein the inspired volume of the first breath after an air pulse has an air to drug aerosol ratio of from about 1:1 to about 2:1.

33. A method of delivering a drug to the lungs of a patient comprising administering said drug to a patient capable of normal breathing without mechanical assistance and having an established unassisted breathing cycle, wherein said administration includes an inhalation phase during which a normal inspired volume of gas is inhaled and an exhalation phase during which a normal volume of gas is exhaled, comprising the steps of aerosolized the drug to produce a selected volume of drug aerosol and delivering the selected volume of drug aerosol to a plenum during the patient exhalation phase; delivering the selected volume of drug aerosol from the plenum to the patient as the first part of the inspired volume of gas on the inhalation phase; and delivering a volume of air which makes up the latter part of the inspired volume of gas for inhalation by the patient into the lungs in conjunction with the patient's natural unassisted breathing; and wherein said method is not practiced in conjunction with a respirator or ventilator.

34. The method for delivering a drug as claimed in claim 33 which further comprises the step of generating a signal related to the exhalation phase of the patient's breathing cycle; aerosolizing the drug to produce a selected volume of drug aerosol and delivering the selected volume of drug aerosol to a plenum during the patient exhalation phase in response to the generated signal.

35. The method for delivering a drug as claimed in claim 33 which further comprises delivering a volume of drug aerosol to the plenum equal to about ¼ to ½ of the Patient's inspired volume of inhaled gas.

36. The method for delivering a drug as claimed in claim 33 which further comprises the step of delivering a volume of drug aerosol to the plenum equal to about ⅓ of the patient's inspired volume of inhaled gas.

37. The method of delivering a drug as claimed in claim 33 including the steps of providing a patient interface, connecting said patient interface to a flexible inhalation tube and a flexible exhalation tube, providing a check valve in said exhalation tube to prevent inhalation therethrough, providing a first filter, connecting the inlet of said filter to said exhalation tube and the outlet of said filter to atmosphere, providing an apparatus to aerosolize said selected volume of drug and deliver said aerosolized drug to said plenum, providing a second filter with an inlet connected to ambient air and an outlet having a check valve through which said volume of air introduced into said plenum, and providing a control unit for pulsing said air entrained drug in a cycle synchronous with said patient's exhalations.

38. The method for delivering a drug as claimed in claim 33 including the step of providing said patient interface in the form of a mask covering the patient's mouth and nose area, providing a mouth piece within and extending through said mask and being connected to said inhalation and exhalation tubes, and providing said mask with a connection to a filter to capture any of said drug should the patient cough.

39. The method for delivering a drug as claimed in claim 33 wherein said apparatus to aerosolize said drug comprises a nebulizer.

40. The method for delivering a drug as claimed in claim 33 including the step of providing a sealable containment case, and locating said first and second filters, said plenum and said aerosolizing apparatus within said containment case.

41. The method for delivering a drug as claimed in claim 33 including the step of programming said control unit to initiate a pulse during each patient's exhalation.

42. The method for delivering a drug as claimed in claim 33 including the step of programming said control unit to provide at least one exhalation between pulses.

43. The method for delivering a drug as claimed in claim 33 wherein said drug comprises at least one toxic drug.

44. The method for delivering a drug as claimed in claim 33 wherein said patient is chosen from the class consisting of a human patient and an animal patient.

45. The method for delivering a drug as claimed in claim 33 wherein the inspired volume of each breath has an air to drug aerosol volume ratio of from about 1:1 to about 3:1.

46. The method for delivering a drug as claimed in claim 45 wherein the inspired volume of each breath has an air to drug aerosol volume ratio of from about 1:1 to about 2:1.

47. The method for delivering a drug as claimed in claim 33 wherein the inspired volume of the first breath after each delivery of drug and air to the plenum has an air to drug aerosol volume ratio of from about 1:1 to about 3:1.

48. The method for delivering a drug as claimed in claim 47 wherein the inspired volume of the first breath after each delivery of drug and air to the plenum has an air to drug aerosol ratio of from about 1:1 to about 2:1.

* * * * *